United States Patent [19]

Horrobin

[11] 4,393,049

[45] Jul. 12, 1983

[54] TREATMENT FOR OBESITY

[75] Inventor: David F. Horrobin, Montreal, Canada

[73] Assignee: Efamol Limited, London, England

[21] Appl. No.: 272,082

[22] Filed: Jun. 10, 1981

Related U.S. Application Data

[63] Continuation-in-part of Ser. No. 89,293, Oct. 30, 1979, Pat. No. 4,302,477, which is a continuation-in-part of Ser. No. 4,924, Jan. 19, 1979, Pat. No. 4,373,763.

[30] Foreign Application Priority Data

| Jan. 23, 1978 | [GB] | United Kingdom | 2642/78 |
| Feb. 7, 1978 | [GB] | United Kingdom | 4921/78 |
| Apr. 19, 1978 | [GB] | United Kingdom | 15481/78 |
| Aug. 17, 1978 | [GB] | United Kingdom | 33682/78 |
| Oct. 24, 1978 | [GB] | United Kingdom | 41761/78 |

[51] Int. Cl.$^3$ .................. A61K 33/30; A61K 31/315; A61K 31/20; A61K 31/33
[52] U.S. Cl. .................................... 424/145; 424/246; 424/271; 424/312; 424/318; 424/289
[58] Field of Search ............... 424/145, 318, 289, 271, 424/246, 312

[56] References Cited

U.S. PATENT DOCUMENTS

| 1,926,745 | 9/1933 | Klopfer | 424/145 |
| 3,923,982 | 12/1975 | Lamand et al. | 424/145 |
| 4,034,099 | 7/1977 | Bryan | 424/271 |
| 4,058,594 | 11/1977 | Williams | 424/312 |
| 4,237,118 | 12/1980 | Howard | 424/145 |

FOREIGN PATENT DOCUMENTS

| 2272684 | 1/1975 | France | 424/271 |
| 7500325 | 12/1975 | France | 424/312 |
| 1391449 | 4/1975 | United Kingdom | 424/271 |

OTHER PUBLICATIONS

*Lancet,* Apr. 30, 1977, p. 936.
*Chem. Abstr.,* vol. 77, 1972, 39210h; 83, (1975), 15501b; 83, 26534r.
U.K. Publication, *Here's Health,* p. 10, 1977.

*Primary Examiner*—Frederick E. Waddell
*Attorney, Agent, or Firm*—Cushman, Darby & Cushman

[57] ABSTRACT

Use of γ-linolenic acid and related materials alone or with zinc or β-lactam antibiotics to treat obesity.

14 Claims, No Drawings

TREATMENT FOR OBESITY

CROSS REFERENCE TO RELATED APPLICATIONS

This application is a continuation-in-part of my earlier application Ser. No. 89,293 filed Oct. 30, 1979, now U.S. Pat. No. 4,302,477, which itself is a continuation-in-part of my earlier application Ser. No. 4,924 filed Jan. 19, 1979, now U.S. Pat. No. 4,373,763.

FIELD OF THE INVENTION

This invention relates to the treatment of obesity primarily, but not exclusively, in the field of human medicine.

GENERAL BACKGROUND

Considerable interest has been shown in recent years in the use of prostaglandin (PG) precursors in medicine. For various reasons it is not practical to administer naturally-occurring prostaglandins such as PGE 1 and PGE 2 to patients. Consequently, considerable attention has focussed on the use of prostaglandin precursors including linoleic acid (9,12-octadecadienoic acid), γ-linolenic acid (6,9,12-octadecatrienoic acid) and dihomo-γ-linolenic acid (5,8,11-eicosatrienoic acid), conversion in the body being believed to be as follows:

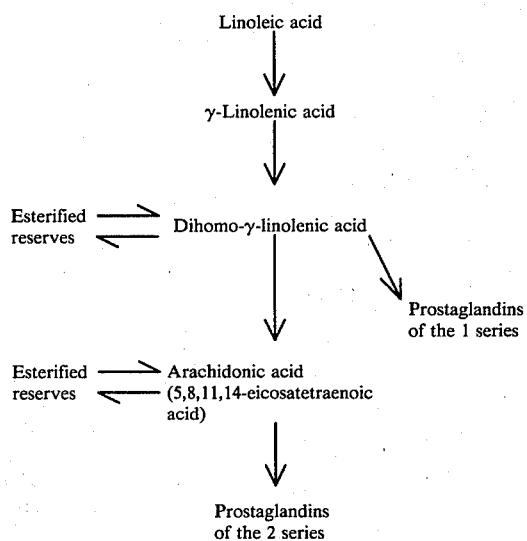

DESCRIPTION OF THE PRIOR ART

Prior art within this general area includes the following patents and papers.

(i) U.S. Pat. Nos. 3,993,775 (issued Nov. 23rd, 1976) and 4,058,594 (issued Nov. 15th, 1977) of John Williams, which describe a method of providing an immuno-suppressive effect in a patient undergoing organ or tissue transplant or suffering from multiple sclerosis comprising administration of a daily dosage of from 5 mg to 3 g of γ-linolenic acid or dihomo-γ-linolenic acid or a functional derivative thereof.

(ii) British Patent Specification No. 1,082,624, published Sept. 6th, 1967, (Calmic Limited), which discloses effectiveness of γ-linolenic acid in the treatment of vascular diseases.

(iii) McCormack, Neil and Sim (The Lancet, page 508, Sept. 3rd, 1977), who describe preliminary work on the use of an oil containing a mixture of linoleic acid and γ-linolenic acid (as triglycerides) in the treatment of rheumatoid arthritis.

(iv) Sim and McCraw (Thrombosis Research Volume 10, pages 385-397, 1977), who describe activity of the methyl esters of γ-linolenic acid and dihomo-γ-linolenic acid in vitro and in vivo on blood platelet function in non-human primates and in man.

(v) French Patent Specification No. 2 272 684 (Ito), which discloses enhancement of antibiotic action by sundry unsaturated fatty acids including [α−] linolenic acid.

PRESENT INVENTION

The present inventor has discovered a number of new applications of γ-linolenic acid and dihomo-γ-linolenic acid in therapy, alone and in conjunction with zinc, β-lactam antibiotics or other materials influencing the 1-series/2-series PG balance in the body in favour of 1-series PG's, herein referred to as 1-series PG enhancers and fully discussed later. These applications are to treatment of obesity as set out in detail herein.

The present inventor believes that this disorder is due to a deficiency of PGE 1 and other PG's of the 1-series, or an imbalance in the normal ratio of 1-series and 2-series PG's.

This has led to the realisation that the precursor(s) which can be used to stimulate the natural production of 1-series PG's in the treatment of the disorder include γ-linolenic acid and/or dihomo-γ-linolenic acid, either or both of which may be used in association with linoleic acid and if desired other fat acids. Although these substances are 2-series PG precursors (via arachidonic acid) as well as 1-series PG precursors, this is not deleterious to their use, although one may require to use relatively higher amounts of precursors than would be the case if only 1-series PG's were being biosynthesized.

Accordingly there is provided a method of treating obesity in a patient which comprises administering to the patient an effective amount of γ-linolenic acid and/or dihomo-γ-linolenic acid, optionally in association with linoleic acid and if desired other fat acids, said acids being used, if desired, as physiologically functional derivatives thereof and optimally with a conjoint amount of a 1-series PG enhancer as referred to above.

A preferred daily dosage for an adult (weight ca 75 kg) is from 0.05, 0.1 or 0.5 g up to 1, 2, 5 or even 10 g as required of γ-linolenic acid or equivalent weight (calculated as γ-linolenic acid) or physiologically functional derivative thereof. Amounts may in particular be 0.1 to 1.0 g daily. In place of, or in addition to, γ-linolenic acid, one may use dihomo-γ-linolenic acid or a physiologically functional derivative thereof, in amounts equivalent in molar terms to γ-linolenic acid and calculated as such. This dosage can for example be taken as a single dose or divided into 2, 3, or 4 subdivisions thereof as convenient.

ANTIBIOTICS

β-lactam antibiotics which may be used in the method of the present invention, are conveniently any of the known penicillin and cephalosporin antibiotics (including semi-synthetic antibiotics) such as, for example, penicillin G, penicillin N, penicillin V, cephalexin, cephalothin, ampicillin, amoxycillin, cloxacillin and cephaloglycin. Any of these may be used in the form of their physiologically functional non-toxic derivatives, for example alkali metal salts e.g. sodium and potassium salts, and salts with organic bases, and reference to an antibiotic herein (including the claims) includes reference to such derivatives.

The antibiotics may for example be administered orally, parenterally or rectally as desired.

The antibiotic is preferably administered in the form of dosage units. Suitable daily dosages of said active ingredient may for example be in the range 0.5 to 3.0 g per day in patients of average weight. Such daily dosages may conveniently be divided into for example, two, three or four equal doses to be administered two, three or four times daily respectively.

The use of penicillins in long term treatment is especially desirable in view of the known relative absence of side effects of these drugs. Thus, penicillin has been administered for many years to patients having rheumatic heart disease in order to prevent streptococcal infections, and there is virtually no evidence of long term toxicity.

Care should of course be taken to ensure that the patient is not allergic to the drug of choice.

If it is not desired to have compositions comprising both a 1-series PG enhancer and the γ-linolenic or other acid or derivatives, the active materials may be given by separate administration in the appropriate relative amounts.

OBESITY

A current technique for the treatment of obesity involves the administration of linoleic acid, generally in the form of vegetable oils such as sunflower oil and/or corn oil. In order to be effective, these current dietary approaches to the treatment of obesity require the intake of other fats in the diet to be substantially reduced. In the body, linoleic acid is converted as described earlier, and the present inventor believes that the beneficial effect of administration of linoleic acid is due to enhancement of 1-series PG production and in particular of PGE 1, this substance causing a metabolic shift increasing appetite and reducing weight. However, the presence of other fats in the diet interferes with the conversion of linoleic acid to γ-linolenic acid and thus reduces the effectiveness of the treatment.

What is now proposed is administration of γ-linolenic acid and/or dihomo-γ-linolenic acid as effective in the treatment of obesity, even when other fats are present in the diet.

DIETARY COMPOSITIONS

The invention is chiefly described in terms of pharmaceutical compositions, but it will be understood that the γ-linolenic and other acids, being in the nature of dietary supplements, could if available at an economic price be incorporated in a dietary margarine or other foodstuff; such foodstuffs are also referred to herein as dietary compositions.

VETERINARY APPLICATIONS

It will be understood that where a disorder of a kind calling for treatment in animals arises, the invention while described primarily in terms of human medicine and treatment is equally applicable in the veterinary field.

Thus for example domestic cats have an unusual dietary requirement in essential fatty acids, being apparently unable to convert linoleic acid to γ-linolenic acid and dihomo-γ-linolenic acid to arachidonic acid. They are liable to a group of related skin conditions with hair loss, dandruff, scaling, pruritis, easy breakdown of the skin with rubbing or scratching, and defective healing, all of which can also be produced experimentally by an EFA (essential fatty acid) deficient diet, evidencing their related nature. Similar conditions can be produced experimentally in other animals, with skin lesions similar to eczema and psoriasis. Feeding of γ- or dihomo-γ-linolenic acid is effective in reversing the conditions, including, perhaps surprisingly, those in cats. This indicates, in view of the arachidonic acid block, that the conditions are indeed, as the present inventor believes also for the human conditions discussed above, related to 1-series PG deficiencies. The spontaneous conditions observed in cats are for example relieved by giving 0.5 g of Oenothera oil per day, five days a week.

FORMS AND SOURCES OF γ-LINOLENIC AND OTHER ACIDS

Convenient physiologically functional derivatives of γ-linolenic acid or dihomo-γ-linolenic acid for use according to the invention for all purposes described include the $C_1$–$C_4$ alkyl (e.g. methyl and ethyl)esters and the glycerides of the acids.

If desired, pharmaceutical compositions may be produced for use in the invention by associating natural or synthetic γ-linolenic acid (or a physiologically functional derivative thereof) and/or dihomo-γ-linolenic acid (or a physiologically functional derivative thereof) as such, with an acceptable pharmaceutical vehicle. It will however generally be convenient to incorporate the γ-linolenic acid into compositions in the form of an available oil having a high γ-linolenic acid content.

At the present time known natural sources of oils having a high γ-linolenic acid content are few (there are no known natural sources of significant amounts of dihomo-γ-linolenic acid). One source of oils currently available is the seed of Evening Primrose species such as *Oenothera biennis L.* and *Oenothera lamarckiana*, the oil extract therefrom containing γ-linolenic acid and linoleic acid in the form of their glycerides together with other glycerides. Another source of γ-linolenic acid is the seed of Borage species such as *Borago officinalis* which, though its current yield per acre is low, provides a richer source of γ-linolenic acid than Oenothera oil. Recent studies on fungi which can be cultivated by fermentation promise a fungal oil source.

The seed oil extracts referred to above can be used as such or can if desired be fractionated to yield an oily composition containing the triglycerides of γ-linolenic acid and linoleic acid as the only fatty acid components, the γ-linolenic acid content being a major proportion. Seed oil extracts appear to have a stabilising effect upon any dihomo-γ-linolenic acid or physiologically functional derivative thereof incorporated therein.

USE OF 1SERIES PG ENHANCERS GENERALLY AND ZINC IN PARTICULAR

As has been mentioned above, γ-linolenic acid and dihomo-γ-linolenic acid function as precursors for both 1- and 2-series PG's. The present inventor believes it advantageous if the biosynthesis of 1-series PG's can be effected preferentially to that of 2-series PG's in many conditions in which 1-series PG imbalances or lack need to be corrected.

It has previously been believed that selective enhancement of 1-series PG formation and inhibition of 2- series PG formation are impossible because the mobilisation of DGLA reserves and the mobilisation of AA reserves have been thought to be the same reaction, mediated by the same phospholipase. Similarly the formation of 1-series endoperoxides from DGLA, leading to 1-series PG's has been thought inseparable from the formation of 2-series endoperoxides from AA, leading to 2-series PG's. The inventor however has evidence that these assumptions are not true and that agents may be found which regulate the reactions selectively; for example penicillin and zinc appear to activate DGLA mobilisation without effecting AA mobilisation and the formation of 1-series PG's is increased preferentially.

Most broadly, agents effective according to the invention are those which:

(a) selectively activate DGLA mobilisation or conversion to endoperoxides, with small or no effect on AA mobilisation or conversion;

(b) inhibit conversion of DGLA to AA. (The body can make up any lack of AA from reserves to maintain 2-series PG production if required);

(c) selectively inhibit AA mobilisation or conversion to endoperoxides, with small or no effect on DGLA mobilisation or conversion.

The materials referred to earlier herein as '1-series PG enhancers' that is to say materials influencing the 1-series/2-series PG balance in the body in favour of 1-series PG's, are thus believed to act by one or more of the above mechanisms.

ZINC

Without restriction to the theory, the present inventor believes that zinc is an example of materials that tend to stimulate the biosynthesis of 1-series PG's and specifically that it potentiates mobilisation of esterified reserve of dihomo-$\gamma$-linolenic acid. This enables one to use zinc conjointly with $\gamma$-linolenic acid and/or dihomo-$\gamma$-linolenic acid.

Based on present evidence, a suitable daily dosage of zinc for an adult (weight ca 75 kg) is 2.5–800 mg preferably 10–200 mg and advantageously 10–80 mg zinc daily, with $\gamma$-linolenic acid or other acid or equivalent in the amounts previously discussed. The 10–80 mg zinc is approximately 0.125–1.0 mg/kg adult body weight. In view of the conjoint effect of the zinc preferred amounts of $\gamma$-linolenic or other acid or equivalent are less than when zinc is not present, advantageously 0.1 to 1.0 g daily. As before the dosage can be taken as a single dose or divided into 2, 3 or 4 subdivisions thereof.

Conveniently the zinc or other 1-series PG enhancer and the $\gamma$-linolenic or other acid or derivatives are given together in a single preparation but they can of course be taken separately.

Zinc should be administered in a form in which it is readily taken up in vivo. Ordinarily this will indicate the use of a zinc salt of a mineral or organic acid, said salt being physiologically acceptable at the given dosage. Some zinc salts which would be contra-indicated at higher dosages may be satisfactory for present purposes at the dosages indicated above. Useful salts include zinc sulphate and zinc gluconate and in particular zinc oleate, $\gamma$-linolenate and dihomo-$\gamma$-linolenate, and zinc oxide may also be employed. It is also possible to administer the zinc in chelated form. In any event, the preferred amounts of zinc are as stated above (the quantities given being calculated as zinc metal).

USE OF $\beta$-LACTAM ANTIBIOTICS

The use of $\gamma$-linolenic or other acids and derivatives, with $\beta$-lactam antibiotics, is discussed above. The present inventor believes that the reason for the effectiveness of the antibiotics is that, as he believes with zinc, they enhance utilisation of ester reserves of dihomo-$\gamma$-linolenic acid. Whether or not this is so, and no restriction to the theory is intended, zinc and antibiotics do appear to have parallel effects in treating all the conditions discussed herein when used with the $\gamma$-linolenic or other acid and derivatives. The compositions may further be expected to be effective in the methods of treatment described in the prior patents and other publications referred to.

It is also, further possible and has been found valuable to use both zinc and $\beta$-lactam antibiotic conjointly with the $\gamma$-linolenic acid, dihomo-$\gamma$-linolenic acid or derivatives as described earlier.

In all cases the amounts of active materials are as discussed already and association of the $\gamma$-linolenic or other acid with linoleic or other fat acids is possible.

Methods of treatment with the addition of an effective conjoint amount of $\beta$-lactam antibiotic, particularly penicillin V, with or without zinc are thus all within the invention, and the $\beta$-lactam antibiotics may of course be used with additional 1-series PG enhancers other than zinc.

PHARMACEUTICAL PRESENTATION

The compositions as administered are conveniently in oral, rectal, parenteral or topical form in a suitable pharmaceutical vehicle, as discussed in detail for example in U.K. Patent Specification No. 1,082,624 and in any case known generally according to the type of preparation. Thus for example tablets, capsules, ingestible liquid or powder preparations, creams and lotions for topical application, or suppositories, can be prepared as required.

Advantageously a preservative such as $\alpha$-tocopherol is incorporated into the preparations. $\alpha$-Tocopherol in a concentration of about 0.1% by weight has been found suitable for the purpose.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The following Examples serve to illustrate the invention:

EXAMPLES

Pharmaceutical compositions containing a unit dose of an oil extract from the seeds of *Oenothera biennis L.* optionally with methyl dihomo-$\gamma$-linolenate and/or zinc sulphate and/or penicillin V are prepared by encapsulation of the natural oil in soft gelatin capsules manufactured by known methods.

The oil is extracted from the seeds by one of the conventional methods of extraction such as cold pressure, screw pressure after partially cooking the seed, or solvent extraction.

Fractionation of a typical sample of this oil shows a yield of 97.0% oil in the form of methyl ester, with the relative proportions:

Palmitate: 6.15
Stearate: 1.6
Oleate: 10.15
Linoleate: 72.6
γ-linolenate: 8.9

As preservative, α-tocopherol is added to the oil in a concentration of 0.1%.

Gelatin capsules containing oil extracts prepared as described above, each having the following contents of active ingredients (0.5 g oil extract=ca 0.045 g γ-linolenic acid), are prepared in conventional fashion. The zinc may conveniently be incorporated as zinc oleate made by the method disclosed in Monatschrift 42 287 (1921) and similar methods may be applied to make for example zinc γ-linolenate if desired.

EXAMPLES, OBESITY

EXAMPLE 1

Oil extract: 0.5 g
Zinc sulphate: 10 mg

Two capsules may be administered thrice daily in the treatment of obesity giving a daily dose of γ-linolenic acid of ca 0.27 g. Capsules without zinc or with double the amount are an alternative.

EXAMPLE 2

Oil extract: 0.5 g
Methyl dihomo-γ-linolenate: 10 mg
Zinc sulphate: 10 mg

Two capsules may be administered thrice daily in treatment as in Example 1, capsules without zinc being an alternative.

EXAMPLE 3

Oil extract: 0.5 g
Penicillin V: 0.25 g

Two capsules may be administered thrice daily in treatment as in Example 1.

EXAMPLE 4

Oil extract: 0.5 g
Penicillin V: 0.25 g
Zinc sulphate: 10 mg

Two capsules may be administered thrice daily in treatment as in Example 1.

EXAMPLE 5

Oil extract: 0.5 g
Methyl dihomo-γ-linolenate: 10 mg
Penicillin V: 0.25 g
Zinc sulphate: 10 mg Two capsules may be administered thrice daily in treatment as in Example 1.

EVIDENCE, TREATMENT OF OBESITY

Thirty-eight healthy subjects took Oenothera oil in 0.6 ml capsules for 6–8 weeks, thirty-four of them at 6 capsules a day and four at eight capsules a day, while continuing to eat their normal diets.

Twenty-two of the subjects, all taking 6 capsules a day, were initially within 10% of their ideal body weight according to the standard life tables. None gained or lost more than 2 kg.

The other sixteen subjects were all more than 10% above their ideal body weight. Of this group, two women and three men showed no change in weight. They were taking 6 capsules a day. Six women and five men lost weight, as follows:

Initial mean weight kg: 74.55±7.94 (S.D.)
Final mean weight kg: 70.42±6.52 (p±0.5. paired t test)

Of the subjects who lost weight, four who were taking 8 capsules a day lost 8.2, 10.0, 10.9 and 12.7 kg respectively. All the other subjects who lost weight were taking 4 or 6 capsules a day.

These results indicate that overweight individuals, but not those of normal weight, have a good chance of losing weight by simple inclusion of Oenothera oil in the diet, and that the weight loss is dose related.

No adverse effects were observed. The intake of 6 capsules a day, 3.6 ml of the oil, is equivalent to ca 0.27 g of γ-linolenic acid; of 8 capsules a day, 4.8 ml of the oil, ca 0.36 g of γ-linolenic acid.

Preliminary results with a further group of subjects indicate improvement in terms of weight loss and proportion of subjects responding, when capsules containing 20 mg zinc sulphate in addition to the oil are used.

EXPERIMENTAL BACKGROUND, USE OF ZINC

Substantial clinical results are not at present available but the present inventor believes, without wishing to be limited to the theory, that at the root of all the conditions lies a fault in prostaglandin metabolism whereby PG's of the 1-series are lacking or their balance with 2-series PG's is upset. From evidence such as that listed below the inventor believes that zinc increases formation of 1-series PG's selectively, apparently by mediating the mobilisation from ester resources of dihomo-γ-linolenic acid.

Thus zinc is indicated in the conditions described herein, as favouring 1-series PG synthesis specifically from administered γ-linolenic acid and related materials.

In one group of experiments the test preparation was the isolated superior mesenteric vascular bed, taken from male rats as for example described in the Canadian J. Physiol Pharmacol 54: 357, 1976. The perfusion flow rate was at a constant value between 3 to 4 ml/min., pressure 25 to 30 mm Hg, using Krebs bicarbonate buffer containing in mM 150 Na, 4.3 K, 1.0 Mg, 2.5 Ca, 1.7 phosphate, 25 bicarbonate and 11.1 glucose.

Prior to testing the basic vasoconstrictive effect of norepinephrine, as the bitartrate, in successive 10 ng amounts was established, as the amplitude of a transient rise of about 1 min in the perfusion pressure.

Zinc, as the chloride, was then added to the perfusion buffer at successive concentrations and the norepinephrine response measured after 15 minutes at each.

The following results were obtained.

| Zinc concentration (μg/ml) | Response as % of basic level |
| --- | --- |
| 0.1 | 112 |
| 0.2 | 118 |
| 0.4 | 130 |
| 0.8 | 138 |

In the presence of 50 μg/ml of indomethacin, a known blocking agent for PG synthesis, used with 10 ng/ml PGE 2 to give apparently normal vascular reactivity, the zinc had no effect on the norepinephrine response.

Similar tests with dihomo-γ-linolenic acid and PGE 1 gave respective rises up to a maximum of 130% of the basic response at 50 ng/ml of the acid and a maximum of 150% of the basic response at $2.8 \times 10^{-11}$ M PG.

The results show that zinc gives responses like those of dihomo-γ-linolenic acid and of PGE 1, responses moreover which are not given when PG synthesis is blocked and PGE 2 supplied, and thus that conditions treated with γ-linolenic acid (and thus effectively with dihomo-γ-linolenic acid) may be enhanced in the direction of 1-series PG synthesis by the addition of zinc.

BACKGROUND USE OF ANTIBIOTICS

On tests carried out as above, both penicillin V and penicillin G have given responses similar in kind and degrees to those given for zinc, supporting further inventor's belief that β-lactam antibiotics are of value in conditions treated according to the invention in similar way to the action of zinc.

I claim:

1. A method of treating obesity comprising administering to a person suffering therefrom an effective amount of γ-linolenic acid or physiologically functional derivative thereof and/or dihomo-γ-linolenic acid or physiologically functional derivative thereof.

2. A method according to claim 1, wherein the daily amount of γ-linolenic or dihomo-γ-linolenic acid or derivatives thereof is 0.05 to 10 g calculated as γ-linolenic acid.

3. A method according to claim 1, wherein the daily amount of γ-linolenic or dihomo-γ-linolenic acid or derivatives thereof is from 0.1 to 5 g calculated as γ-linolenic acid.

4. A method of treating obesity comprising administering to a person suffering therefrom an effective amount of (a) γ-linolenic acid or physiologically functional derivative thereof and/or dihomo-γ-linolenic acid or physiologically functional derivative thereof, and (b) a conjoint amount of a material influencing the 1-series/2-series PG balance in the body in favour of 1-series PG's.

5. A method according to claim 4, wherein said material (b) is physiologically assimilable zinc.

6. A method according to claim 5, wherein the daily amount of the active components is from 0.05 to 10 g of (a) calculated as γ-linolenic acid and from 2.5 to 800 mg of (b).

7. A method according to claim 5, wherein the daily amount of the active components is from 0.1 to 5 g of (a) calculated as γ-linolenic acid and from 10 to 80 mg of (b).

8. A method according to claim 4, wherein said material (b) is a β-lactam antibiotic.

9. A method according to claim 8, wherein said antibiotic is a natural or semi-synthetic penicillin or cephalosporin antibiotic.

10. A method according to claim 8, wherein said antibiotic is selected from pencillin G, penicillin N, penicillin V, cephalothin, ampicillin, amoxycillin, cloxacillin, cephalexin and cephaloglycin.

11. A method according to claim 8, 9 or 10, wherein the daily amount of the active components is from 0.05 to 10 g (a) calculated as γ-linolenic acid and 0.5 to 3 g of (b).

12. A method according to claim 8, 9 or 10, wherein the daily amount of the active components is from 0.1 to 5 g (a) calculated as γ-linolenic acid and from 0.5 to 3 g of (b).

13. A method of treating obesity comprising administering to a person suffering therefrom an effective amount of (a) γ-linolenic acid or physiologically functional derivative thereof and/or dihomo-γ-linolenic acid or a physiologically functional derivative thereof and conjoint amounts of (b) physiologically assimilable zinc, and (c) a β-lactam antibiotic.

14. A method according to claim 5 or 13 wherein the zinc is present as zinc oleate, zinc γ-linolenate or zinc dihomo-γ-linolenate.

* * * * *